United States Patent
Janssen et al.

(10) Patent No.: US 10,042,981 B2
(45) Date of Patent: Aug. 7, 2018

(54) METHOD AND APPARATUS FOR SUPPORTING TASK SCHEDULING IN A RADIATION THERAPY WORKFLOW VIA PREDICTION OF CRITICAL WORKLOAD

(71) Applicant: KONINKLIJKE PHILIPS N.V., Eindhoven (NL)

(72) Inventors: Marco Henricus Maria Janssen, Valkenswaard (NL); Thomas Netsch, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 124 days.

(21) Appl. No.: 15/038,589

(22) PCT Filed: Nov. 25, 2014

(86) PCT No.: PCT/EP2014/075499
§ 371 (c)(1),
(2) Date: May 23, 2016

(87) PCT Pub. No.: WO2015/082253
PCT Pub. Date: Jun. 11, 2015

(65) Prior Publication Data
US 2016/0300024 A1  Oct. 13, 2016

(30) Foreign Application Priority Data
Dec. 4, 2013 (EP) ..................... 13195719

(51) Int. Cl.
G06F 9/46 (2006.01)
G06F 19/00 (2018.01)
G06Q 10/06 (2012.01)
G06F 9/50 (2006.01)
G16H 40/20 (2018.01)
G06Q 50/22 (2018.01)

(52) U.S. Cl.
CPC .............. *G06F 19/327* (2013.01); *G06F 9/50* (2013.01); *G06F 19/3481* (2013.01); *G06Q 10/06* (2013.01); *G16H 40/20* (2018.01); *G06Q 50/22* (2013.01)

(58) Field of Classification Search
None
See application file for complete search history.

(56) References Cited

U.S. PATENT DOCUMENTS 5,586,021 A * 12/1996 Fargher ............ G05B 19/41865
700/100
6,546,073 B1 4/2003 Lee
7,647,130 B2 * 1/2010 Fischer .................. G06Q 10/04
700/105

(Continued)

*Primary Examiner* — Wissam Rashid

(57) ABSTRACT

A method and related system for supporting task scheduling. Completion times of tasks of a process are predicted based on historical data held in a database (HIS). Based on the predictions, a workload measure for a resource associated with performing the task is computed. Also, there is established whether the predicted completion times will result in overshooting predefined due-dates as held in a rules database (DB-REG). The work load measure and/or the overshoot is indicted as graphical indicators in a graphical user interface (GUI). The workload measure and/or the overshoot indicators are computed and displayed in real-time.

14 Claims, 11 Drawing Sheets

(56) References Cited

U.S. PATENT DOCUMENTS

| | | |
|---|---|---|
| 7,801,270 B2 | 9/2010 | Nord et al. |
| 9,727,829 B2 * | 8/2017 | Bollapragada ....... G06Q 10/043 |
| 2004/0010437 A1 * | 1/2004 | Kiran .................... G06Q 10/06 705/7.14 |
| 2004/0267575 A1 | 12/2004 | Boing |
| 2005/0222971 A1 * | 10/2005 | Cary .................... G06Q 10/109 |
| 2005/0283387 A1 * | 12/2005 | Donoghue ............ G06F 19/322 705/3 |
| 2007/0185731 A1 | 8/2007 | Reynolds et al. |
| 2008/0152085 A1 | 6/2008 | Saracen et al. |
| 2008/0195452 A1 | 8/2008 | Ponce De Leon |
| 2009/0037242 A1 * | 2/2009 | Ventura ................. G06Q 10/06 705/7.24 |
| 2010/0005473 A1 | 1/2010 | Blanding et al. |
| 2010/0257015 A1 | 10/2010 | Molander |
| 2011/0238440 A1 | 9/2011 | Leuschner |
| 2013/0085343 A1 | 4/2013 | Toimela et al. |
| 2013/0145092 A1 * | 6/2013 | Miwa ..................... G06F 3/061 711/114 |
| 2013/0304496 A1 | 11/2013 | Rangadass |

* cited by examiner

| Patient Name | ID | Oncologist | Target Area | Protocol | Process | Satus | Priority | Due Date | Message | First RT fraction |
|---|---|---|---|---|---|---|---|---|---|---|
| Brent, Louie | 79024 | Peronel, Tamara | Lung | BR-47 | Record and verify | To do | not set | not set | | not set |
| Hollie, Sabrina | 78073 | Peronel, Tamara | Lung | BR-47 | Image import | In progress | not set | not set | | 2013-11-06 |
| Joselyn, Nola | 29431 | Everard, Benjamin | Bladder | BL-11 | Treatment request | To do | 2 | 2013-10-21 | | 2013-10-25 |
| Palmer, Alex | 22609 | Everard, Benjamin | Bladder | BL-11 | Record and verify | To do | 0 | 2013-10-23 | | 2013-11-01 |
| Rayes, Ike | 15160 | Everard, Benjamin | Lung | BR-36 | Imaging | To do | -1 | 2013-10-21 | | To do |
| Temple, Jeanette | 37998 | Peronel, Tamara | Lung | BR-47 | Contouring oncologist | In progress | not set | not set | | |

Fig. 6

| Monday | Tuesday | Wednesday | Thursday | Friday | Saturday | Sunday |
|---|---|---|---|---|---|---|
| 30 | 1 | 2 | 3 | 4 | 5 | 6 |
| 7 | 8 | 9 | 10 | 11 | 12 | 13 |
| 14 | 15 | 16 | 17 | 18 | 19 | 20 |
| 21 2 | 22 2 | 23 [3] | 24 [3] | 25 [3] | 26 | 27 |
| 28 2 | 29 2 | 30 2 | 31 2 | 1 2 | 2 | 3 |

710 (pointing to 21 cell); 712 (pointing to 28 cell)

Fig. 7

| 800 | 802 | | 804 | | 806 | |
|---|---|---|---|---|---|---|
| Benjamin Everard | 0,84 | Administrator | 0,84 | Joselyn Nola | 2 | Final Consulation |
| Brent Osborn | 0,0 | Management Staff | 0,0 | Rayes Ike | 1 | Image Import |
| Brittany Kelcey | 0,34 | Med Phys | 0,84 | Palmer Alex | 2 | Treatment Planning |
| Cammie Lita | 0,34 | Med Phys in Training | 0,34 | Total number of due-dates | 3 | |
| Georgine Lavender | 0,84 | Radiation Oncologist | | | | |
| Koby Malcom | 0,34 | Radiation Oncologist in Training | | | | |
| Natalie Liliano | 0,34 | Red Tech | | | | |
| Tamara Peronel | 0,0 | | | | | |
| Tom Waldo | 0,0 | | | | | |
| I | | II | | III | | IV |

Fig. 8

↗All workflows ▫Add Patient ⇌ All workflow Templates ⇌ Add new workflow Templates ✱ Settings ▼ ⇌ Management Reporting ⁞≡ Worklist ▼

Due-Date Thresholds

| User-Thresholds | User-Thresholds (Priority) | Day-Thresholds | Role-Thresholds |
|---|---|---|---|
| User-threshold yellow [3] | Patient threshold yellow [1] | Day threshold yellow [4] | Role threshold yellow [4] |
| Defines number of due-dates when indications are shown in yellow. | Defines number of days when indications are shown in yellow. | Defines number of due-dates when indications are shown in red. | Defines number of due-dates when indications are shown in red. |
| User-threshold yellow [3] | User-threshold red [-1] | Day threshold red [5] | Day threshold red [5] |
| Defines number of due-dates when indications are shown in red. | Defines number of due-dates when indications are shown in red. | Defines number of due-dates when indications are shown in red. | Defines number of due-dates when indications are shown in red. |

Display enabled
☐
Enables red, yellow and green indications on site.

[Save]

Fig. 10

METHOD AND APPARATUS FOR SUPPORTING TASK SCHEDULING IN A RADIATION THERAPY WORKFLOW VIA PREDICTION OF CRITICAL WORKLOAD

CROSS-REFERENCE TO PRIOR APPLICATIONS

This application is the U.S. National Phase application under 35 U.S.C. § 371 of International Application Serial No. PCT/EP2014/075499, filed on Nov. 25, 2014, which claims the benefit of European Patent Application No. 13195719.3, filed on Dec. 4, 2013. These applications are hereby incorporated by reference herein.

FIELD OF THE INVENTION

The invention relates to a method of supporting task scheduling, to a system of supporting task scheduling, to a computer program element, and to a computer readable medium.

BACKGROUND OF THE INVENTION

The optimal scheduling of processes in a manufacturing or clinical process can be challenging since constraints from various resources have to be considered. Other complexities arise because already approved processes may need to be adapted due to delays etc. Automatic schedulers are oftentimes found either too expensive for large scale applications or their responsiveness does not allow them to be used in fast paced environments.

SUMMARY OF THE INVENTION

There may therefore be a need for an alternative method and related apparatus or system for helping a user when scheduling processes.

The object of the present invention is solved by the subject matter of the independent claims where further embodiments are incorporated in the dependent claims. It should be noted that the following described aspect of the invention equally apply to the system of supporting task scheduling, to the computer program element and to the computer readable medium.

According to a first aspect of the invention there is provided a method of supporting task scheduling, the method comprising:

receiving a request for a process of a type, the process comprising a sequence of tasks to be performed by one or more of a plurality of resources;

based on historical data, predicting a completion time of a later one of the tasks, given a starting time for a previous one of the tasks.

According to one embodiment the method further comprises:

re-predicting the completion time of the later task once any one of the previous tasks in the process or in a co-pending process of the same type has been completed.

According to one embodiment the method further comprises:

updating the historical data once one or more or all tasks of the process or of a co-pending process of the same type have been completed.

According to one embodiment the method further comprises: establishing whether the predicted or re-predicted completion time for the later one of the tasks complies with a predefined time constraints for instance a completion period for said task. For instance, the predefined or prescribed completion period may set a mandatory maximum for an allowable lag between two tasks that need be observed.

According to one embodiment the method further comprises:

predicting respective completion times for two tasks including the later task, the method further comprising:

establishing whether the predicted completion times comply with a predefined lag period between the two tasks.

According to one embodiment the method further comprises:

for said later task and for a corresponding task in a co-pending process of the same type, accumulating task completion times that i) fall within a given interval and/or ii) are to be performed by or for the same resource and then computing a workload measure for the resource from the accumulated completion times.

In one embodiments the predicted future workload are used in the step of establishing whether or not the prescribed lag- and/or completion periods are met, that is, whether or not an "overshoot" may occur. In a medical context, for instance in radiation therapy planning, patients, who are currently passing through a workflow (process), are automatically identified when overshoots in their workflow are predicted to occur.

According to one embodiment, the workload measure is predicted or computed in real-time upon any one of i) receiving the (initial) request for the process, ii) updating the historical data, iii) updating time constraints applicable to the process type and iii) updating the completion time of any previous task in the process or in the co-pending process. The prediction of future workloads (for resources such as staff member and equipment) and/or due date overshoots (in respect of prescribed time constraints) allows (hospital) organizations to pro-actively take action when upcoming bottlenecks are identified from the predictions. In other words, and in one embodiment, the method affords automatic and real-time predictions of future workloads for staff members and equipment resources based on historical data and workflow protocol templates.

According to one embodiment the method further comprises: displaying on a graphics display a visual indication of the workload measure wherein the visual indication varies with the real-time predicted workload measure and/or comprises displaying on a graphics display a visual indication of the amount by which the completion time does not comply with the predefined completion period and/or the predefined lag time, wherein the visual indication varies with the amount of non-compliance.

According to one embodiment the graphics display includes a calendar component and wherein the visual workload measure indication is mapped onto said calendar component.

According to one embodiment the method the displaying of the graphics display is effected in real-time upon any one of i) receiving the request for the process, ii) updating the historical data, iii) updating time constraints applicable to the process type and iv) updating the completion time of any previous task in the process or in the co-pending process.

It is envisaged in one embodiment, that the re-predicting of the remaining completion times are triggered once an actual completion time (of tasks(s) in the current process of or task in any co-pending process of the same type) has been updated and then the display of workload and or due date compliance is then updated accordingly This allows accounting for delays that may occur in the completion of tasks. In other words, the one or more re-predictions of a given task for a process may differ from prediction to predication as the (re-)predictions are always based on updated historical data that take the latest information of actual, that is confirmed, completion times of task of the certain process types into account.

According to one embodiment the workload measure for the resource is classified into any one of a plurality of criticality levels according to a classification scheme, wherein the displaying of the workload measure includes displaying the applicable criticality level, wherein the classification scheme is user customizable. The classification scheme includes coding or "modulation" of the visual indicators by color and/or shape and/or size. For instance, a traffic light scheme may be used to indicate the raising level of criticality by green, amber and red. The customizability as proposed herein allows the graphics display (such as a graphical user interface GUI) "to be adapted to site specific understanding of when the predicted load on a resource is considered well below maximum capacity ("ok"), is it about average ("busy"), or is "very busy" (that is, critical)" so would next to exhaust the maximum capacity of said a resource. It is envisaged herein the method can be applied to various sites and each site may perform the classification scheme customization by itself independently from other sites and for each resource separately.

According to one embodiment, the resource includes a device wherein the device is any one of i) medical imaging modalities, ii) dedicated treatment preparation workstation and iii) radiotherapy treatment devices, linear accelerators, low- and high dose rate brachytherapy devices etc.

In sum, the method as proposed herein includes retrospective, learning-based estimation of due dates. It does not implement however the actual scheduling, but it allows quickly verifying whether a given scheduling plan is like due to lead to bottleneck because of undesirable accumulation of predicted due dates. It allows users to quickly identify resource bottlenecks, that is, whether a newly registered patient workflow would put pressure on the current schedule of other patients, staff members, days and devices. At any time, a number of key performance parameters (e.g. number of patients with overshot prescribed lag-times, average and max. workload for each or user selected ones of the resources) of the actual state can be derived and the staff can be warned if operations in the RT department get under pressure since many "due dates" are predicted to accumulate at a certain (group of) resource(s) and/or whether prescribed time constraints such as inter-task lag-times and task or workflow completion periods are met at the predicted due dates.

Resources as used herein are defined broadly and includes devices/equipment (such as a Linac (linear accelerator), a contouring workstation) which or by which a respective one of the tasks is to be performed. But also staff members or staff roles may be considered as resources. Also, entities on or in respect of which the tasks are carried may be considered resources. Also the time intervals or "slots" that are used to schedule the tasks (for instance, days, hours, minutes) may be looked at as resources. A resource herein is anything that imposes a constraint on the task to be carried out. For example, a piece of equipment may only handle a limited number or jobs per day or hours and so does a staff member. Or, looked at it the other way around, a defined time interval or slot (date/day or hour slot) may only accommodate a limited number of tasks. Similarly, there is a limit to the number of tasks that can be performed on a patient within a defined time interval, because of travel time for instance between different sites where two different tasks can be performed. The term "resources" as used herein then comprises different categories of time intervals (e.g. a calendar date), a staff member, staff role, or equipment, or the patient. It is a feature then of the method as proposed herein to map or "focus" the predicted completion time across one or more of the different resources categories and to express the work load measure in terms of or in respect of either one of the resource categories or to cross-check the predicted completion times against prescribed due-dates to identify possible overshoots. Workload or due date focused views of selected ones of the resources can be produced.

BRIEF DESCRIPTION OF THE DRAWINGS

Exemplary embodiments of the invention will now be described with reference to the following drawings wherein:

FIG. 6 shows a graphical user interface according to a second embodiment;

FIG. 7 shows a graphical user interface according to a third embodiment including a calendar component;

FIG. 8 shows a graphical user interface according to a fourth embodiment;

FIG. 10 shows a graphical user interface according to a sixth embodiment;

DETAILED DESCRIPTION OF EMBODIMENTS

Figure 1:
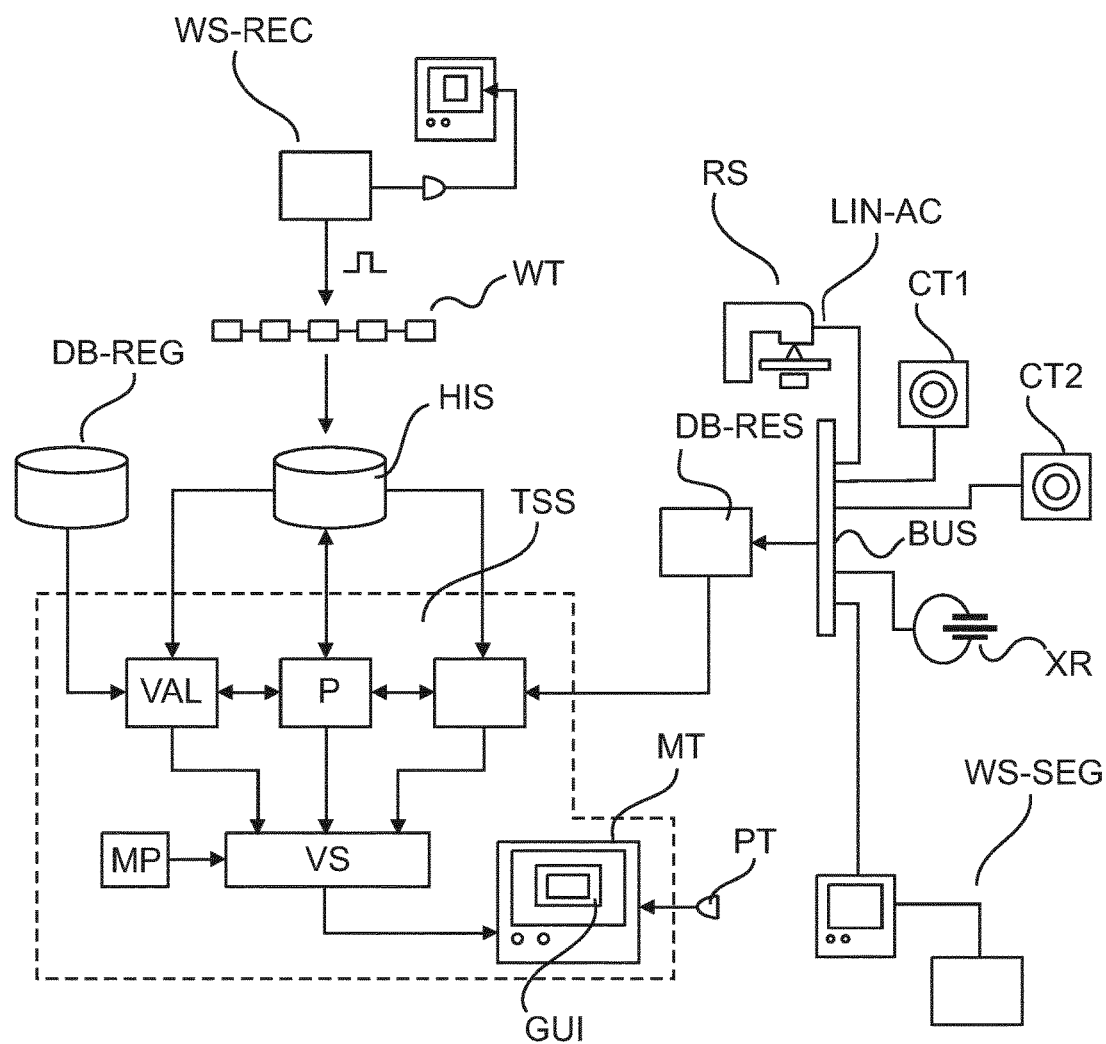
FIG. 1 shows a system for supporting task scheduling.

With reference to FIG. 1, there is shown a block diagram of a process management system PMS for managing usage of a plurality of resources RS. The resources include, for instance, medical equipment such as linear accelerators LIN-AC, x-ray CT scanners CT1,2, planar x-ray equipment XR, and/or computer workstations that run special modules such a segmenter tools, or include a combination of any of the previous items. However, this listing of resources is purely exemplary and in no way limiting, and other resources (equipment, human knowledge, the patient, etc.) are likewise envisaged herein.

Operation of the process management system PMS will be explained in the following in a medical context, more particularly in the context of radiation therapy planning, preferably, but not only, in a distributed clinical environment. Again, this context is in no way limiting and is merely an example for an application scenario for the processor management system as proposed herein. For instance, it is envisaged that the processor management system PMS can likewise be put to good use in a manufacturing context.

Figure 2:
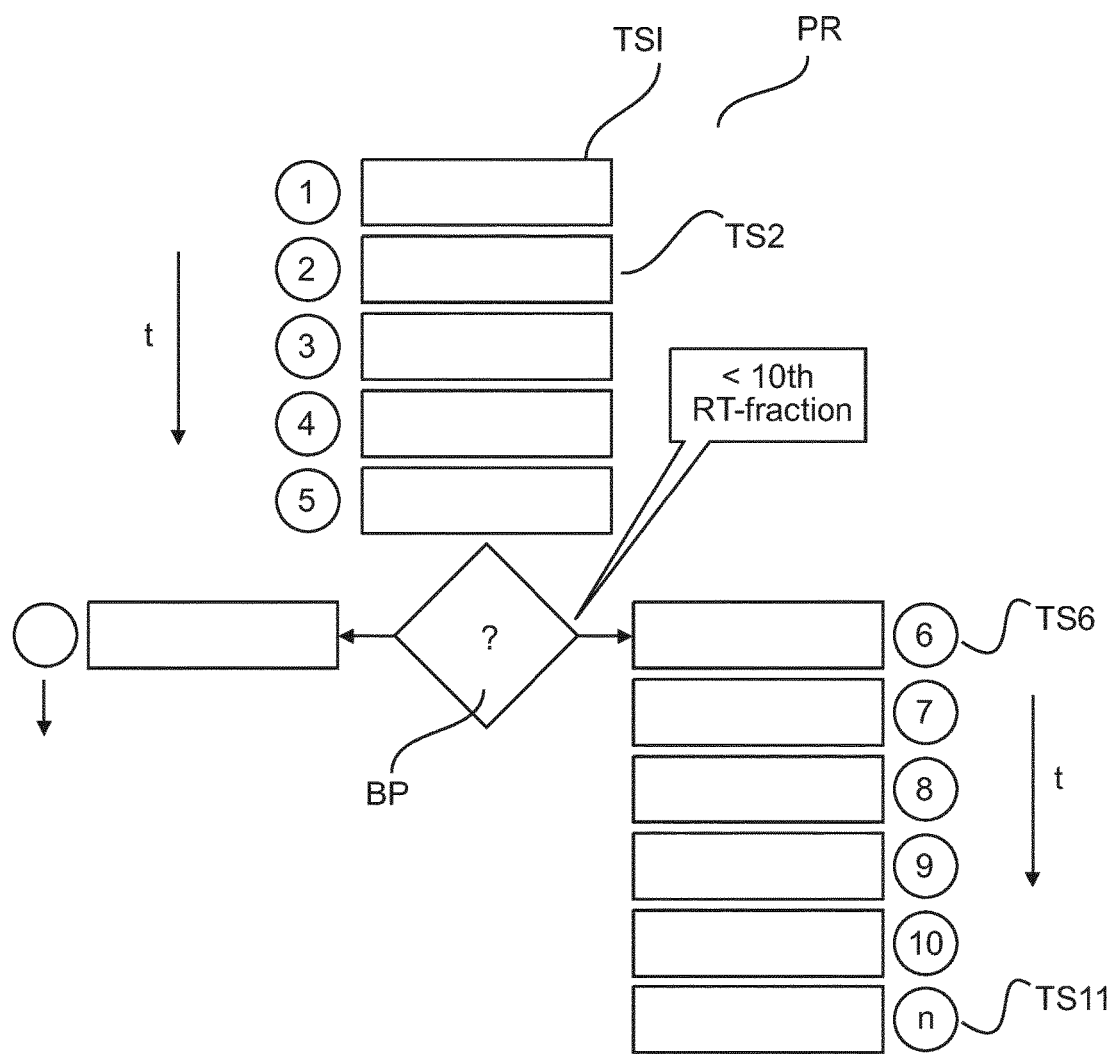
FIG. 2 shows an example of a work flow or process template.

The conceptual representation of a "process" (also referred to herein as workflow) is shown in FIG. 2. The process includes a number of separate tasks (also referred to herein as "steps"). More particularly, FIG. 2 shows a type of a radiation therapy planning process in flow chart notation. Radiation therapy (RT) generally calls for a complex patient workflow protocols that includes in one exemplary embodiment, the following tasks TS (numbered in FIG. 1 as TS1-11) of planning (preparation), evaluating, delivering and monitoring patient treatment as it progressed from task to task. Depending on the treatment type (e.g. photon, proton), target area (e.g. prostate, lung), treatment fractionation scheme (e.g. 20 fractions of 1.8 Gy) and possible co-morbidities, an optimal (patient specific) treatment workflow WS is selected (FIG. 1). Two workflows can be said to be of the same type if their flowchart (the one in FIG. 2 is an example) share the same structure. For instance, patients who suffer from the same form of cancer, say lung cancer, will in general have workflows set up that are of the same type.

Each individual workflow step TS1-TS11 involves one or more of resources RS such as a suitable treatment window at the linear accelerator ("linac") LIN-AC for treatment delivery, the contouring of tumors and risk organs at a treatment planning workstation with segmentation tools WS-SEG or a slot in a mould room needs to be booked so a technician can carry out special patient preparations prior to treatment. Also, operation of the equipment sometimes requires attendance by a suitably qualified staff, such as a radiation oncologist.

Figure 3:
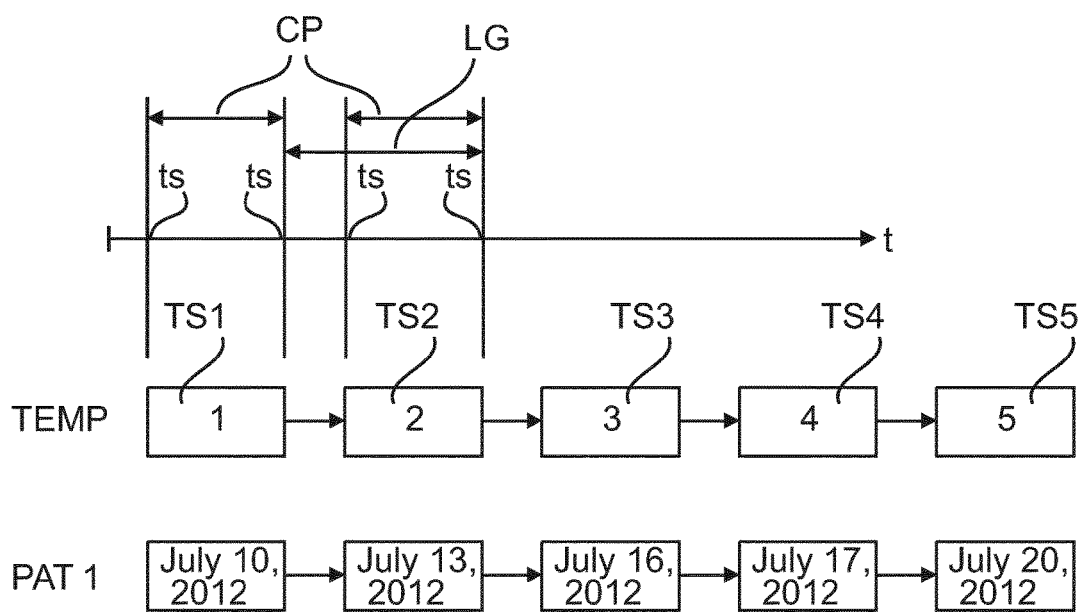
FIG. 3 shows terminology in connection with the process template in FIG. 3.

Referring now to the upper part of FIG. 3, there is shown an example a template TMP for a process comprising five tasks labeled TS1-TS5. FIG. 3 illustrates some chronological terminology that will be useful in the following explanations. Each task TS has its semantics and its chronology. The semantics defines what needs to be done by which equipment. The chronology includes certain time constraints respect of that task. The chronology includes a completion period CP. The completion period CP is defined by a starting time ts of the respective task and by the completion time tc. Between any two tasks, for instance task TS1 and TS, there is a lag period (or delay or simply "lag") which is the difference between the completion time tc of previous task TS1 and the completion time tc' of a follow-up task TS2. The completion time ts of the last task (shown in the illustration as TS5) is the completion time of the whole process. In general, if concurrency is allowed, and if there is no strict causality (so a follow task TSi does not necessarily require all inputs from tasks with lower index TSj (j<i)) the completion time of the whole process is then the completion time of the last task to complete. There is also a completion period for the whole process which can be defined from the chronology terms introduced above. The completion period or duration for a process is defined as ts(TS1)–tc(TS_last), that is the time difference between starting time of the initial or first task TS1 and the final task TS_last which is usually the task with the highest template index k (in FIG. 3, k=5). Similarly, a completion period or duration can be defined for each task TSi as ts(TSi)–tc(TSi).

The workflow template TMP can be encoded by a suitable data structure such as a referential data structure or a nested XML file with each node representing one of the steps TS. Each node then includes identifiers, that is strings, that each encode the equipment to be used, the nature of the task to be carried out, and may also include information of the task's chronology. Each node includes an entry to receive a time-stamp which indicates the completion time tc of the individual task. The lag LG defines the maximum allowable delay between the completion times tc of two consecutive tasks. In other words, tc+LG for any task defines the "due date" for when the completion of the follow up task falls due. Although a uniform notation ts, tc, LG is used herein, this is for convenience only and it is understood that the ts, tc, LG may be different (but not necessarily) for each or for any two task(s). The tasks of a process are in general connected in that the later task takes as input the output of the earlier task. The lag may then be thought of as a "rubberband" that interconnects the tasks and represents a certain completion time tolerance to better accommodate changes when scheduling the process, on which more later.

The lower portion is an example of a workflow template PAT1 registered for a patient with each task node populated with respective completion times. In other words, this template represents "historical data" in that it represents the "footprint" of a past workflow that has been completed, that is, the patient has been progressed through the whole sequence of tasks and each task has been completed according to the time stamp as recorded in the exemplary template. Such templates can be produced by a hospital information system that registers the respective time stamp by using suitably programmed event handlers that respond to completion signals for a specific patient. The completion signal carries the respective time stamp and is issued by the respective resource equipment after completion of the respective task. Issuance of the signal is either automatic or after operation of an "OK" actuator by authorized staff that oversee execution of the respective task. Over time, completed templates from different patients are accumulated in the HIS maintained database and form a stockpile of historical information on the chronology of each workflow type and it is proposed herein to Hamas this historical data to predict the chronology of future workflows of the same type.

As mentioned earlier, operation of the processor management system PMS is not restricted to the medical context. For instance, in a manufacturing context each task may correspond to a manufacturing task. For instance, in polymer processing, one task may represent an injection molding and a follow up task involves surface finishing of the injection molded product. The lag then indicates the maximum allowable time period within which the surface finishing step needs to commence once the product has been injection molded. For instance, if a pattern is to be cut into the surface of the injection molded product, this must commence within a certain lag period for otherwise the surface of the product cures out and it may no longer be possible to apply the cuttings.

To maximize patient throughput in an RT department whilst still aiming for both, optimal treatment outcome for the patient and patient comfort, the usage of resources (such as patients, staff members, devices and equipment) for specific workflow task TS1-11 have to be "optimally" scheduled. Automated scheduling is usually considered challenging exercise in the ever busy clinical environments, in particular because dynamic changes around resources (patient arrives late, a staff member is taken ill, an urgent treatment request is added, a device has downtime, etc.) may necessitate re-scheduling in an already highly constrained schedule.

A more relaxed way of scheduling may only consider "due dates" within a workflow. For example, in the Netherlands, a lag LG between a new treatment request (which may be interpreted as the $0^{th}$, or "seed" task of a workflow) and the first treatment task of a patient may not be longer than 21 days for certain treatment workflows. In other words, after patient registration, the due date for the first treatment task is already known. Within a medical workflow other time constraints are also effective, for example, the requirement that after a medical imaging task, the treatment planning task should be completed within 4 days. Also, the department itself may operate a catalogue of best practice rules and ask for certain tolerable lags between individual workflow steps to minimize patient waiting times.

Broadly, and referring back to FIG. 1, the process management system PMS as proposed herein is configured to automatically derive completion times of the tasks TS within a workflow from historical data. A predictor module P of the process management system PMS retrospectively operates to a statistically analyze the timestamps of all workflow steps of a certain class of workflows for all patients which have previously been treated (that is, for home complete records exist). The processed workflow templates of previous patients are stored in a hospital information systems HIS. Based on the statistical analysis of the processed workflow templates as held in the HIS, the expected completion times of the workflow tasks of a new patient can be statistically predicted (in other words, learned from historical data) and added to a calendar component of a graphical user interface GUI. Various embodiments of such GUIs with calendar components with mapped into completion times are shown in FIGS. 5-8, on which more later.

Already during patient's reception when a request for a new treatment plan is lodged at reception workstation WS-REC (such at a hospital reception desk or remotely requested by the patient's GP) and a new workflow template WT of corresponding class or type is invoked or instantiated, it can be indicated, whether the new patient will increases the "due date load" at a certain day (or other relevant time interval, such as hour, minute, etc.). A combiner or "accumulator"• combines all predicted completion times for all co-pending workflows (of which there can be a lot in large medical centers of major urban conglomerates) at any given day in order to derive criticality measure for the work load for that day. The criticality measure is then mapped by a mapper MP into a suitable color (or gray value) coded indicia and said color-coded indicia are then display on screen MT in a GUI. Also, in one embodiment, the predicted completion times can be automatically checked by a validator VAL against prescribed lag-times LG and overall work flow completion times that are held in a rule database DB-REG. Possible overshoots can then be identified and flagged up in the GUI alongside or instead of the workload indicia. See for instance FIG. 6.

The proposed PMS ensures staff is alerted on possible work overloads or process bottlenecks at an early stage and can then take suitable remedial measures such as attempting to reschedule certain tasks in a patient's workflow where current lags between tasks are not yet stretched to the allowable maximum as prescribed. As will be appreciated from the above, the proposed PMS is not in itself a scheduler, but it helps staff identify quickly (that is, in real-time) days with critical workloads and/or overshoots for any given scheduling arrangement.

Figure 4:
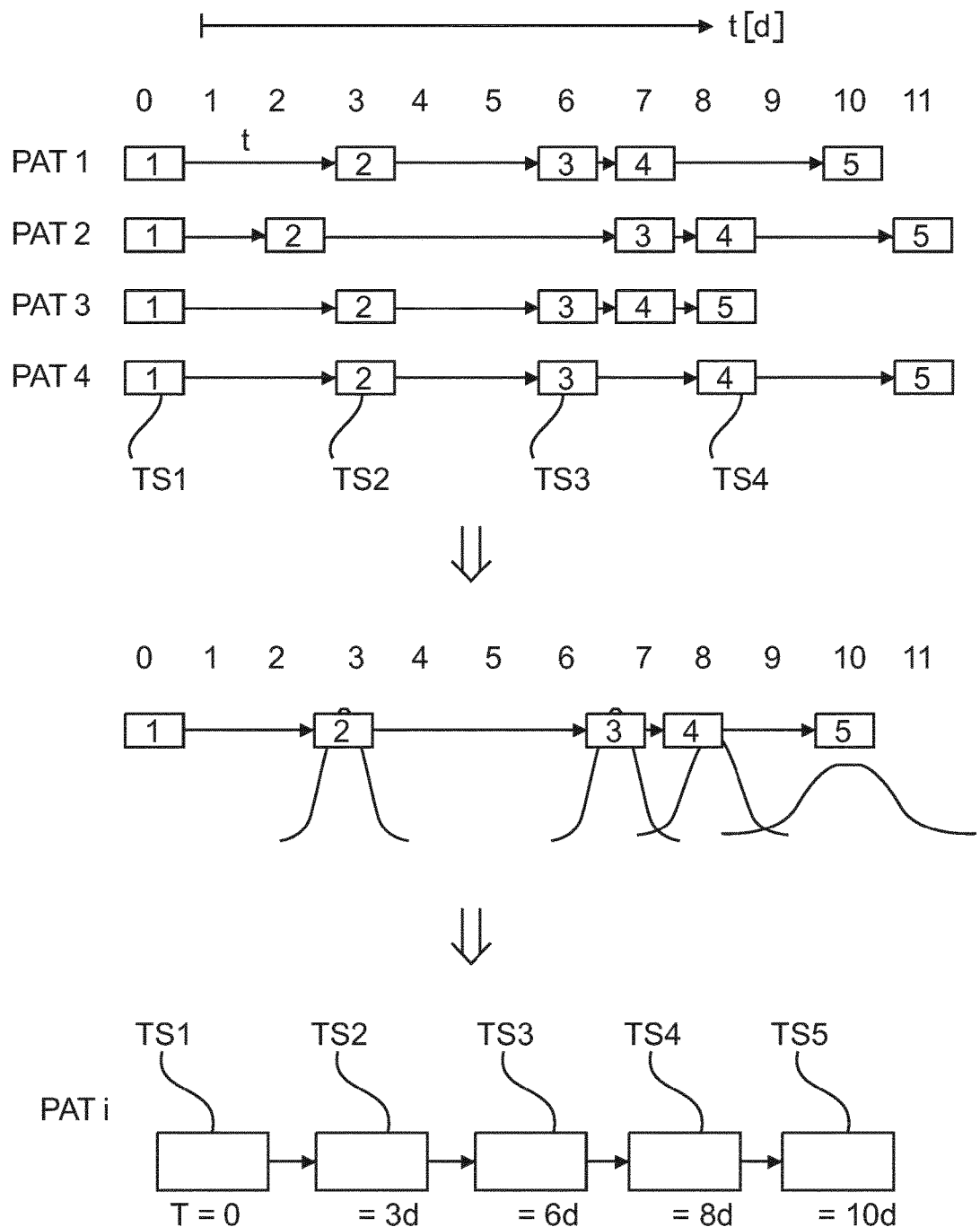
FIG. 4 shows operation of a predictor module as used in the system of FIG. 1.

With reference to FIG. 4 and the lower part FIG. 3, operation of predictor module P will now be explained in more detail. For better illustration, we assume purely for illustrative and explanatory purposes (which is no way limiting to the operation predictor module P), a workflow template WT of a certain class (say lung cancer treatment) with 5 workflow steps TS1-TS5 as shown in the lower part of FIG. 3. In the database of the HIS there, are 4 patients stored for whom said 5 steps-lung cancer-template has been used and concluded in the past. In other words, each workflow items TS1-TS5 for each workflow template task records the completion time (in this case, completion date) at which the respective item TS1-TS5 has been completed.

The lower part of FIG. 3 shows a template PAT1 of a workflow completed in the past, with each entry populated with exemplary completion times for Patient 1. In this case, the completion times are measured in terms of days although this may not be so necessarily as the system proposed may also work with other time scale resolutions such as hours, minutes or even seconds.

The actual completion time (for instance, dates although other time scales such as hours, minutes etc. may be used in other contexts) can be normalized with respect to the first task TS1 and all subsequent completion dates can then be computed as a difference value $\Delta t$ in terms of days with respect to the date of initial workflow step TS1, as shown in the upper part of FIG. 4. From this "$\Delta$" representation, an average or expected completion date for each subsequent step TS2-TS5 for the instant workflow template class can be estimated once a suitable family of probability densities is assumed for the events of interest (in this case, completion dates). In one embodiment a Gaussian distribution/density is assumed as shown in the middle part of FIG. 4 where the probability densities for the respective task completion dates are shown for illustration. The most likely completion date of a workflow step can then be considered as a reasonable estimate or "prediction" due date for a new patient as exemplary shown in the lower part of FIG. 4. As will be appreciated from the above the conditioning with respect to a given completion date implements a statistical estimation procedure based on conditional expectation.

For instance, given the workflow is currently at the initial step TS1, the completion date for the follow up step TS2 can be predicted to be 3 days later as exemplary shown in the lower part of FIG. 3 in view of the average estimates for the Gaussian densities as shown in the middle part of FIG. 3. Based on the statistical analysis outlined above, predictor P can then predict the completion date for any desired downstream step TS2-TS4. For instance, step TS3 can be expect to complete at 6 days after the initial step TS1 and so on. However, the prediction can be conditioned or normalized with respect to any desired step TSi so conditioning is not necessarily with the respect to the initial step TS1 for a given workflow template but the prediction may be conditioned with respect to completion time of a downstream task TS1+j. However, conditioning the prediction with respect to the initial step for a given workflow class has the benefit that the predictor P is able to predict the completion dates for any of the follow-up tasks at a very early stage, that is, once a workflow template has been invoked for the given patient which may happen as early as upon registration of the patient.

Indeed, in a preferred embodiment, the previously described prediction is not a one-off operation but a re-prediction is triggered for a given, pending workflow once a completion date for a downstream task TS1+i is lodged with the HIS. In other words and in one embodiment, prediction of the completion dates for the remaining tasks TSi+1+j (j>0) is repeated for each completed workflow step TSi+1. In yet other words, the predictor operates a re-prediction scheme and re-computes the conditional expectations once a respective signal is intercepted informing that a currently pending task has been completed. The predictions are then recomputed but the estimation for the conditional expectation is now conditioned on the fact that the previously pending task TS1+1 has now been completed. Put differently, the normalization or conditioning step previously explained in connection with FIG. 3's upper part for the initial step TS1 is repeated for any completed downstream task TS1+i as the patient progresses through the workflow. This allows better accounting for updates in the historical data. For instance historical data about previously completed workflow tasks of co-pending workflows may have meanwhile accumulated in the historical data in the HIS database. Therefore, the re-predicting operation in response to changes in co-pending workflow templates as registered by the HIS ensures that the (re-)predictions are always or largely based on up-to-date historical data. To enable this real-time responsiveness of the predictor in respect of newly completed tasks in any either the instant workflow or in any of the co-pending workflows of the same class or type, the prediction module is configured as an event driven module that includes a suitable event handler. In other words, the re-prediction operation is triggered once a signal is received from the HIS that a workflow template has been completed for a given patient. In this manner the quality of the estimates can be increased because the system constantly learns from newly completed templates and responds to updates of the historical data in the HIS.

Other embodiments proceed in a more "coarsely grained" fashion in that the re-prediction is not triggered for each and every task reported as completed, but the re-prediction is only carried out once a signal about a completed (co-pending) workflow is received (that is, the signal confirms that each task in the co-pending workflow has been completed).

The signal about task or workflow completion is either automatically issued by the HIS, or an authorized user manually issues such a signal about task for example by setting (via mouse click, keyboard stroke or otherwise) a "completed" flag in an electronic form associated with the template.

It will be appreciated form the above, that a certain amount of historical data will need to be present in the HIS. For newly installed systems, predictor P is envisaged to operate in an "intelligence gathering mode" as opposed to the actual operation where phase described above where predictions are issued. For newly incoming template workflow templates for which there is no sufficient historical data yet, the proposed method can then be gradually applied. In other words, for new patients to whom an unfamiliar workflow has been assigned to, no due date prediction will be issued until a suitable amount of historical data in respect to said new workflow template has accumulated in the HIS database. The conditional expectation estimates are then updated with every completed workflow for the new template. Over time, with an increasing amount of historical data available for the new workflow template, actual due date estimates can then eventually be issued and they are expected to become more stable over time. Alternatively, if such "break-in" or "learning only" periods are undesirable, historical data acquired from another site may be imported for a newly installed one and the stock of imported historical data is then gradually adapted to local behavior over time through on-going update operations as previously described.

The already computed estimates for completion dates per workflow type can be held in the HIS database by installing additional tables or predictor P may maintain its own dedicated database. Absent any updates for a certain workflow type, the operation of the predictor becomes essentially a look-up exercise for a newly incoming workflow request. The predictor P retrieves the most recent completion dates (conditioned on the initial step for the respective workflow type) and forwards same to visualizer VS so they can be accounted for by accumulator• and then mapped into the calendar component to update the work load measure indicator for each of the respective dates on which the predicted completion dates happen to fall.

Although operation of predictor P has been explained above at FIG. 3 for linear workflow templates, more complicated workflows may also be handled. For example, some workflow templates may call for decision points or branch points BP or may allow concurrencies or loops. For example, in case of a branched workflow step, the individual steps in the receptive "yes" and 'no" branch are initially considered as one single step with a single (lumped) distribution and a corresponding coarse estimate for the conditional expectation for a completion date for the whole "yes" or "no" This lumping together (which is essentially a summation over all the conditional densities for workflow tasks in the respective branches) will of course lead to a less accurate prediction in the initial stages of the workflow during the run-up to said branch point BP. But once the branch point uncertainty has been resolved, that is, once the predictor P receives a signal as to which one of the "yes" or "no" branch in a current workflow has been selected, the predictor can then refine the estimation for the steps along the selected branch thus providing better resolution for the estimates of the respective completion dates.

The validator VAL allows considering additional due date constraints within a workflow. Once the completion dates are predicted by predictor P, the predicted completion dates are passed on to validator VAL to have them checked for compliance with prescribed time constraints as currently held on rule database DB-REG. Examples of such time constraints are maximal allowable inter-task lags LG and overall workflow completion times. For instance, one example of a lag constraint is that the first treatment task TS2 of a patient may not be longer than 21 days after registration TS1 of the treatment request. If any overshoot is registered, that is, if it is determined that the prescribed lag is overrun based on the predicted completion times, a warning flag is set in respect to the respective task having non-compliant completion time. This flag can then be used by visualizer VS to effect display of a corresponding indicator on GUI to alert the user to the looming overshoot. In one embodiment, there is also an indicator to indicate that the overall completion time for the whole workflow, based on the currently predicted completion times for the various steps TSi in the workflow, are set to overshoot the prescribed time limit and can be indicated in graphic an/or numerical form as explained earlier in patient focused. See FIG. 6 below for a non-limiting example.

The combiner• is configured to consolidate for each day (or other suitable intervals or slots) the predicted completion times from essentially all co-pending workflows. In one embodiment, combiner• is configured, for each given day, to increment a counter for each predicted completion date that falls onto that day. The sum (or a weighted sum) over those counts per day is then output as work load measure for the respective day. The workload measure is preferably computed in real-time and dynamically adapted to changes in the predicted completion dates. In other words, the completion times are computed from the most recent predicted completion dates. Once a completion time is re-predicted for a task in any one of the pending workflows, a signal is issued by predictor P which is intercepted by an event handler of combiner•. The combiner• then re-computes the workload measure for the respective day. In this manner, the computed workload measures always reflect the latest developments across the various workloads in the clinical facility. The various workload measures per day are then passed on to the mapper MP. Mapper MP then maps the workloads onto a user configurable criticality scale. For instance in one embodiment, the scale is three-tier and includes thresholds for "low", "medium" and "high" criticality. Other thresholding arrangements into fewer or more tiers is also envisaged. The respective thresholds in the criticality classification scheme can be adjusted by the user. In this manner each site can individually, that is for each resource, determine what it considers a critical, medium, or low workload at any the respective device. The term "resource" is used broadly here and is not restricted to the actual medical equipment RS, but also includes staff trained to operate the equipment. The workload criticality measured as furnished by the combiner and the classification of same by mapper MP is equally applicable to individual staff members. The available resources RS, that is, the medical equipment and information about qualification and availability of medical staff are held in a resource database DB-RS which the combiner• and or the mapper MP can query in order to compute the workload criticality measures. For instance, a technician can be expected to attend limited number of imaging sessions per day. As that number is approached by predicted task completion times, so does workload on said technician for the respective day.

It is also envisaged herein that the resources database DB-RS includes up-to-date records on scheduled maintenance downtime of respective equipment items, but also records on holiday or sick leave or others absences for each relevant staff assigned to respective equipment RS or at least to a respective class of equipment (for instance, staff "XX" is trained to operate CT, etc.). By using the information in the resources database DB-RS, the combiner is able to account for how many resources RS are actually available, that is, how many equipment items and how many staff members capable of operating same are actually available on the respective day. For instance if, a member of staff is taken ill and/or a certain item of equipment is down on a specific day, this would increase the criticality measure for remaining equipment and/or staff. In other words, combiner• operates to consolidate information on the actually available resources with the predicted completions per day for the respective work flow tasks. The respective workload for the day and/or resource is then made available to the mapper in order to assign to the respective task and/or equipment and/or staff the respective criticality level.

The output of mapper MP is an associative data structure that associates to each day and/or resource (staff and/or equipment) the respective criticality level. Visualizer VS controls the visual appearance of the GUI on screen MT as a function of the current work load criticality levels as supplied by the predictor-combiner-map processing chain. More particularly, visualizer VS operates to map the recorded criticality levels for each day and/or resource into a calendar component by color and/or shape-coding the levels into visual GUI widgets. As is the case for the predictor and combiner/mapper, the visualizer is also envisaged to operate in real-time in response to changes in the supplied workload criticality levels and to dynamically adapt the visualization of workload criticality indicators in the GUI. For instance, the color and/or shape-coding of the respective indicators varies as the predictor operates to re-predict the completion times and/or the combiner keeps re-computing the respective workload measures in view of updated resources availabilities.

Figure 5:
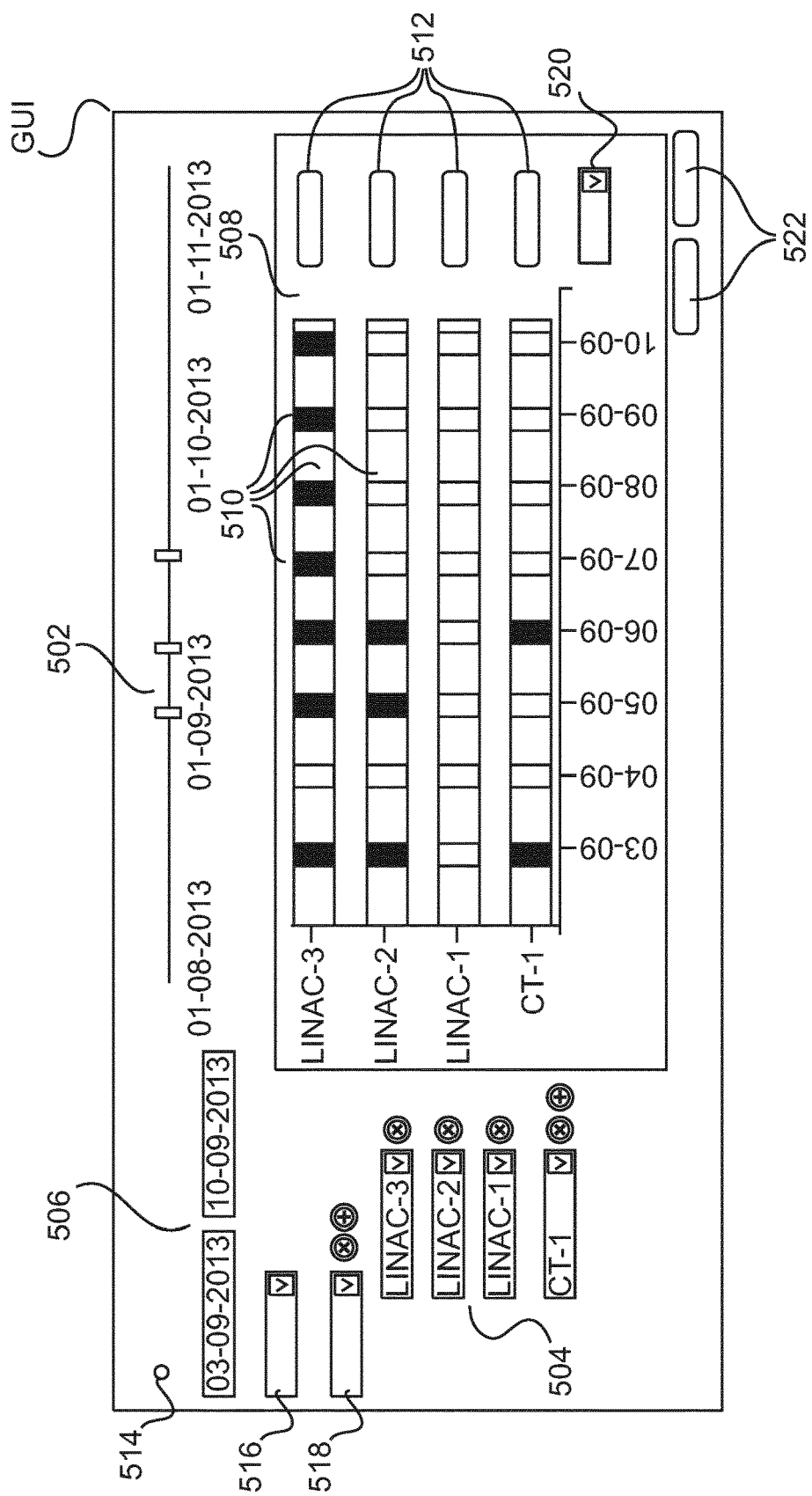
FIG. 5 shows a graphical user interface according to one embodiment as produced by the system in FIG. 1.

Reference is now made to FIG. 5, where a graphical user interface is shown as produced in one embodiment by visualizer VS on screen MT. In the embodiment according to FIG. 5, the predicted completion times of different tasks and the scheduling constraints mentioned, are displayed as "heatmaps" 510 mapped into a one or more time line 508 as the calendar component. A slider widget 502 allows restricting the time range to be considered with time indictors 506 displaying the selected time range. These heatmaps represent the predicted future workloads for, both staff members and equipment RS. From these heatmaps, the hospital department gains insights in possible upcoming critical workloads. FIG. 5 shows a workload heatmaps for 3 treatment devices LINAC-1, LINAC-2 and LINAC-3 as well as for 1 imaging device CT-1 for the period September 3 until September 10. Heatmaps can be generated for each resources: staff members, staff groups (roles), equipment (e.g. imaging and treatment equipment) and types or class of processes (e.g. tumor contouring or treatment planning). The calculation of the heatmaps is based on the predicted completion times as supplied by predictor P as explained above in connection with FIG. 4. The predicted completion time marked up in the heatmap indictors 510 may be that of an individual task or it may be the completion time for the entire process. The workflow task whose heatmap indicators 510 are displayed may be a workflow item TS where the presence of the respective patient is required (such in as medical imaging, treatment or an investigation task), but indicator may also refer to a workflow item 510 where the patient's presence may not be required as it involves a staff number or equipment only such as in e.g. treatment preparation, e.g., contouring. In such cases, staff members work with patient data as held in the HIS.

It should be understand, that the exact design as shown in FIG. 5 is but one embodiment only and variations to the FIG. 5 layout are also envisaged herein. For present purposes, a "heatmap" graphics display arrangement as proposed herein includes a plurality of color- or shape-modulated widgets that are mapped onto a calendar component so that both, i) the workload criticality (in respect of task, resource, etc.) and ii) the predicted completion time is discernible by the user through visual inspection of the GUI's design. The GUI association between dates and work load criticality for staff and/or equipment affords a more effective user machine interaction which helps to further lifetime of delicate and complicated equipment. For instance, in one embodiment, the workload indicators 510 are displayed as bar elements along a timeline at the respective day/date, one timeline for each equipment resource LINAC-1-3 and CT-1. The criticality is color-coded by displaying the indicator bar elements in different colors shown in FIG. 4 in different shading. Although a gray color coding is envisaged in some embodiments, color-coding in more conspicuous colors are preferred to enhance ergonomy. For instance, in one embodiment a traffic-light-color coding is used, where green indicates low criticality level, amber indicates medium criticality level and red indicates a high criticality. As an illustrative example, in the FIG. 3 rendering, criticality varies with shading heaviness, that is, the denser the shading, the higher the work load criticality. So what the user learns from GUI as per FIG. 5 is that at a certain instance there is higher workload demand for linear accelerator LINAC-3 on 3 September than there is for CT imager CT-1. This may indicate that more tasks have been predicted to fall due on 3 September that require the linac than there are tasks that call for CT equipment CT-1,2. In addition or instead, because of the combiners operation, the higher workload may be due to the fact (as established by the combiner through database queries in resource database DB-RS) that there is less staff available for operating the linac on that day than there is staff present versed in the art of using a CT or it may indicate that linac is down for maintenance for some time during that day, etc. As explained previously, combiner• combines the information on the number of predicted completion times with resource availability into a single workload value that is displayed in the color-coding of the respective indicator 510 associated with the respective day. The single workload value measures the criticality of the combined effect of how much demand (=number of predicted completion times) there is on that day and how many resources (=equipment and/or staff) are actually available on that day. In one embodiment, demand and resources are not combined into a single value but combiner provides separate value for each, demand and resources, and mapper MP maps these onto separate criticality levels which visualizer then renders into separate indicator elements. For instance, in this embodiment the indicator bars 510 may be defined as "multibar" elements formed from sub-segments, with each sub-segment then indicating separately the criticality level for demand and resource availability, respectively.

Depending on the embodiment on the GUI, there may also be one or more (or any combination) of the following interactive user functionalities each envokable by a respective button or slider widget. For instance, in one embodiment there is a reset button "today" 514 that upon actuation sets the upper and lower time restrictions 506 to the current day as indicated in the system time. This also changes the time resolution, and the timeline 502,506 switches over into hourly intervals and the GUI now shows the workload criticality mapped into hourly slots rather than resolving as before work load criticality only down to 24 hour slots (that is, "days").

Resource button 518 allows selecting the resources of interest in respect of which the work load criticality is to be displayed. FIG. 5 shows the case where equipment has been selected but user may wish to select "staff" instead whereupon the heatmap is displayed as workload versus staff member roles. Button 504 allows selecting particular resource items such as particular equipment or individual staff members.

Time granularity or resolution button 520 allows changing the time line resolution from days into weekly or monthly blocks or even down into hourly slots (or in some embodiments even down to minutes or seconds). Similar to the reset button 514, changing the time resolution effects a rescaling of the completion times to fit the currently selected time resolution. The amount by which the resolution can be changed is ultimately a function of the time resolution of the time stamps used to record the various completion times or events.

A export button allows converting the GUI views into various file formats such as into spreadsheet format or graphic format etc.

"Calender view" button 512 allows changing into a grid calender view as shown below in FIG. 7 for a respective resource to drill down or break down workload criticality for a particular resource of interest. FIG. 7 affords an exemplary embodiment for a view of workloads mapped into a grid calendar 710 component for a specific resource. Although the calendar component is shown in grid form this is not essential and in other embodiments a linear time line is used as shown in FIG. 5. The heatmap indictors 712 per resource in calendar view indicate the respective number of predicted completion times for each date. The numbers of predicted completion times are indicated as the workload measure with the color-coding indicating the criticality. The indication of the actually number of task completions for the respective day is optional so may be omitted in some embodiments in which case only the color-coding is displayed for each heatmap element 712. In the example of FIG. 7, a lighter shading now indicates higher criticality but the coding is understood as purely illustrative and in no way limiting. For instance, the work load is predicted to be more critical on Wednesday $23^{rd}$ because a demand to complete 3 tasks is predicted for that day whereas a predicted demand for 2 task completions the day before is considered less critical as indicated by the heavier shading for Tuesday $22^{nd}$.

Reference is now made to FIG. 8 which shows a GUI 800 that can be envoked by clicking onto a date in the calendar grid of FIG. 7. The user is then redirected to a view 800 presenting workload indictors 804, 806, 808 in terms of color coding and/or display of the actual number of predicted completion times for each staff member and/or role (that is, a group of staff that can carry out said role) II and/or patient and/or resources and/or workflow type, each shown in columns I-IV respectively. Of course, the order of the columns is immaterial and the particular arrangement in FIG. 8 is for illustrative purposes only. The GUI element 800 is thought to be envoked upon user click on calender grid point Friday 25 on calendar view GUI of FIG. 7. The workload in widget 712 showed a load of three tasks that have been predicted to complete on said day. The 3 tasks can be refound in GUI 800 in FIG. 8 in patient column III as the total of task completion dates but now broken up per patient. The user learns from patient column III that the three tasks are predicted for completion, broken down as one task per patient Nola, Ike and Alex on said day. The completion times may also mapped into other resource representations namely staff in column I, role in column II and workflow type in column IV in order to "focus" the workload on the user selected resource category. In other words, FIG. 8 shows an overview with workload focused on different resources: column I is staff based workload, column II is a staff role based workload, column III indicates patient/subject based workload and column IV is a task type based workload. The order of columns I-IV is of course non-limiting and can be specified by the user. Also, not necessarily all columns I-IV are displayed.

The number of predicted task completion times for the user selected (that is clicked on date) are represented by fractional numbers for the staff column I and the group of staff column II. For example, in the case of predicted task completion times as mapped to roles in column II, a workflow task may be carried out by each staff member assigned to the specific roles. Therefore the exact number of predicted completion times for a task per staff member is the average value workload, that is, the number of tasks is divided by the total number of available staff for the specific role. Again, display of the actual completion time numbers and/or their fractions as per user role is optional and may therefore by omitted so it is only the color coding of the respective labels 804, 806, 808 that furnishes an indication of the workload distribution. In other words, GUI 800 illustrates the functionality of expressing the predicted task completion times not only in terms of tasks, but also in any one of staff, staff role, patient, equipment etc. This functionality of mapping completion times across resource categories can be achieved by using the join operator when querying the various databases in FIG. 1 and using the encoded information in the workflow template to thereby link various resources to the workflow tasks. Each workflow type and the tasks therein are linked not only to the patient but also to the equipment as encoded in the semantics of each task node in the workflow data structure flow. The equipment however is linked to staff qualification and roles. Using this links allows the combiner to query the database accordingly and to then map the completion estimates to single one or a plurality of desired resource categories as exemplary shown in FIG. 8.

Reference is now made to FIG. 6, where a GUI 600 is shown mapped to the patient category according to one embodiment. In this patent list view, the heatmap representation is now not workload focused as previously in the calendar view GUI of FIG. 7, but is due date focused. The predicted completion time for the whole process is cross-checked with the prescribed due-date and overshoot are shown as a "global" (that is applicable for the completion of the whole process) color-coded indictor 605 an/or as numbers where for instance a negative number indicates the days by which the due date is predicted to be overshoot. In case indication is by number and color, the number can be displayed superimposed on the colored indictor 605. For instance one may use the following heatmap palette: green=still some days to go till due-date, orange=perform task today, red=due date overshot. Or numerically, an integer value indicates number of working days to go till due-date (e.g. +2 means two days to go till due date) or numbers of days overshot (e.g. −2, means 2 days overshot). In the patient focused view as per FIG. 6, any one of the following indications or any sub-combination thereof may also be included in some GUI embodiments: There is a patient details column 610 showing name and or ID. Column 630 shows an ID (that is, the type) of the current process as applied to the patient. The task column 640 shows the currently processed task of said process. Status bar 645 indicates whether the task shown in column 640 is ongoing or is still to commence. Due date column 655 shows the applicable due dates as derived from rule database REG-DB. Optionally there is also column to indicate due dates of further tasks that are deemed important to warrant a dedicated column. For instance in one embodiment said column is a "fractionation column". It shows the due date of for the first radiation fraction, that is, the day on which a first portion of radiation is to be administered to the patient. Also in one embodiment there is a target area column 625 indicating the organ to which are currently ongoing task for the next task is to be applied. Column 630 shows the staff column, indicating staff to which the respective tasks have been assigned to. According to one embodiment there is also a priority column 650 which indicates by color and/or numerically the urgency status of the task as per column 645 in terms of the prescribed due date versus the predicted completion time for said task in task column 645. In other words, in one embodiment, there is a "local" due date overshoot indicator 645 for a single task of the process (for instance, the currently processed one) and there is the global overshoot indicator 605 that indicates whether the completion of the overall process (that is, the completion time of the last task in said process) is set to overshoot the prescribed process due date as per the current predictions. In other words, although the overall completion time for the process my not show an "urgent" indication via global indictor 605, the local task specific indicator 650 may still indicate "critical" or "urgent" because of an overshoot caused by a prescribed maximal allowable lag-time with respect to an earlier completed task of the process. For instance, in the example of FIG. 6, the task "imaging" of process BR-36 stands predicted as overshooting its due-date/lag by one day (−"−1") whereas the task "record and verify" of process BL-11 seems on target although another day of delay will run into an overshoot. Similar for the task "imaging request", for which there are still 2 days to go. Instead of or in addition to the respective numerical indicators, each task priority indicator may appear heatmap color-coded (from top to bottom), as green, orange and red or any other suggestive color-palette that is capable of reflecting the urgency/priority.

Figure 9:
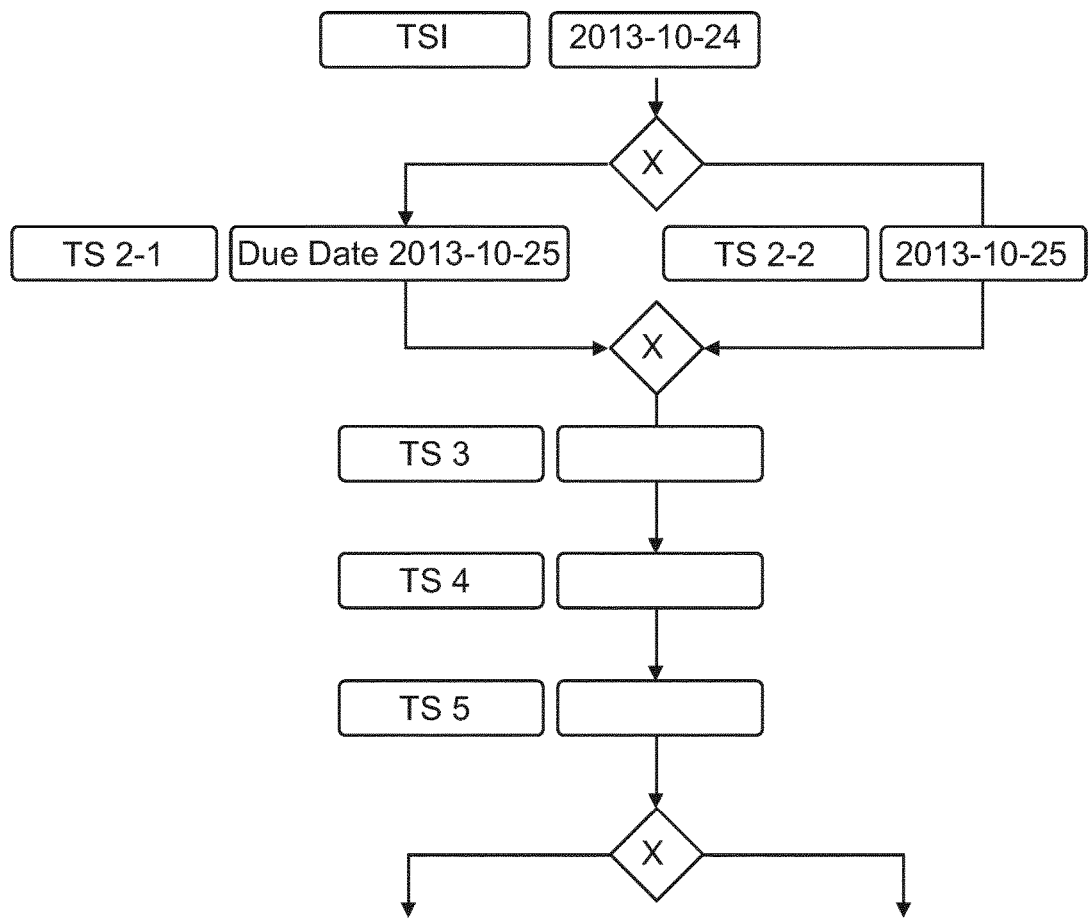
FIG. 9 shows a graphical user interface according to a fifth embodiment.

Reference is now made to FIG. 9 where a user interface is shown as displayed upon instantiating a new workflow template for a new patient. The graphical user interface shows a layout rendering of the workflow type in form of a flow chart with fields. Each field represents a task for the workflow and each field 905 is capable to receive completion date for the respective task. Already when specifying the due-dates for a new treatment workflow, the user is presented with an up-to-date due-date heatmap in the calendar view as shown in the lower part FIG. 9. This allows the user to quickly identify critical situations due to scheduling the new patient. The calendar view per FIG. 7 with heatmaps is phased in as second window and is then displayed together with the workflow layout. In one embodiment, the respective calendar cells have a background color that indicated the workflow measure for the respective day or the calendar day numbers are shown in a corresponding color-coding. The coding is schematically shown as circles around dates (in FIG. 9, the "22" and "23" of October are date flagged up as "critical") with high workload. Whenever a task has been completed, the user may populate the respective field with the actual completion date which triggers a real-time re-prediction of the completion times of the remaining task or tasks of the workflow. The completion times are mapped in real-time into the calendar view to update the heatmaps accordingly.

Reference is now made to FIG. 10 where a user interface representation is shown that supports site specific adaption of the "color coding" for the heatmaps. The user at a specific site (e.g. a hospital) can specify for each color code an individual criticality threshold thereby defining a criticality classification scheme that is to be applied at that site. This allows one site to consider a per-day threshold of 4 task completion times already as "amber" (some pressure) while another site considers this already as "red" (high workload, lot of pressure, action required). In other embodiment, there may also be an option to set the scheme centrally for all or selection of sites.

Figure 11:
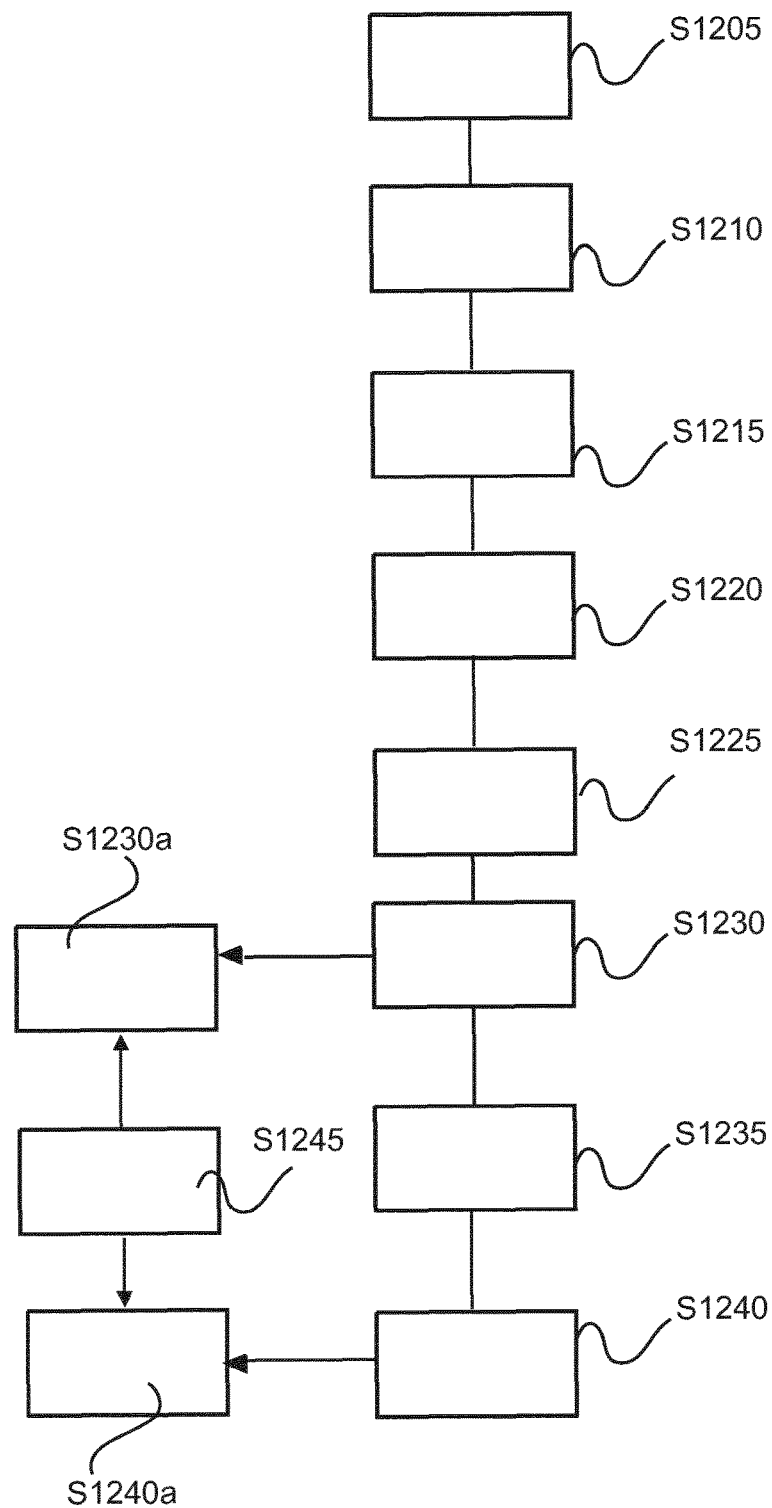
FIG. 11 shows a flowchart for a method of supporting task scheduling.

Reference is now made to flow chart of FIG. 11 where steps of a method of supporting task scheduling are shown.

At step S1205 a request for a type of a process is received. The step comprises a sequence of tasks to be performed by one or more of a plurality of resources.

The process may be for manufacturing an item or may be a medical one, for instance workflow in radiation therapy planning.

At step S1210 a completion time of a later one of the tasks is predicted, given a starting time for a previous one of the tasks. The prediction is based on historical data which include records of previously completed workflows including time stamps on the actually completion of various tasks. The prediction includes a statistical analysis of the data per workflow type to derived estimates for the completion times for said workflow type. In one embodiment, the estimates are conditional expectations conditioned on the event that a certain one of the tasks has been completed.

In one embodiment, the prediction is based on the first or initial step. The initial step may include envoking or instantiating the work flow template of said type in a computer system (such as a HIS) for a new patient in a radiation therapy planning facility.

At step S1215 the completion time of the later task is re-predicted once any one of the previous tasks in the process or in a co-pending process of the same type has been actually completed. By re-predicting based on completion times of actually completed tasks, allows ensuring that the predictions account for delays etc.

At step S1220 the historical data is updated once a task or once all tasks of the process have been completed. The updated may also be triggered by task completions in co-pending processes of the same type. In this way, the historical data can be kept up-to-date and any (re)-predictions is thereby ensured to correctly reflect the latest developments.

At step S1225 it is then established whether the predicted or re-predicted completion time for the later one(s) of the tasks complies with a predefined completion period for said task. It will be appreciated, that step S1225 is repeated once a re-prediction has occurred as the re-predictions of the very same task in a process may vary from prediction instance to prediction instance and therefore the outcome at step S1215 on whether there is or there is no due date compliance may vary also.

According to one embodiment, respective completion times for two tasks including the later task are predicted and at step S1230 it is established whether the predicted completion times comply with a predefined lag period between the two tasks.

At step S1235: for said later task and for a corresponding task in a co-pending process of the same type, accumulating task completion times that i) fall within a given interval and/or ii) are to be performed by or for the same resource.

At step S1240 a workload measure is computed for the resource from the accumulated completion times.

In one embodiment, the workload measure is computed in real-time upon any one of i) receiving the request for the process, ii) updating the historical data, iii) updating time constraints applicable to the process type and iii) updating the completion time of any previous task in the process or in the co-pending process.

At step S1240a a graphics display is displayed including a visual indication of the workload measure wherein the visual indication varies with the real-time predicted workload measure. In one embodiment, the displaying is effected in real-time, that is, as soon as the predicted workload is available. Instead of or alongside with the workflow displaying step there is displayed at step S1230a on the (or a different) graphics display a visual indication of the amount by which the completion time does not comply with the predefined completion period and/or the predefined lag time. The visual indication varies in with the amount of non-compliance. The two indications on workload and non-compliance with the predefined time constraints can be combined into a single score or measure value which is then displayed. Again, the single measure is envisaged to be displayed in real-time, that is, the displayed value is updated as soon as an update of the single or the two measures (non-compliance and workload) become available.

The displaying of the graphics display at steps S1230a, S1240a is effected in real-time upon any one of i) receiving the request for the process, ii) updating the historical data, iii) updating time constraints applicable to the process type and iv) updating the completion time of any previous task in process or in the co-pending process.

The displaying of the two indications on workload and non-compliance (whether or not consolidated into the single measure value) includes classifying or mapping same into any one of a plurality of criticality levels according to a classification scheme wherein the displaying of the visual indicators includes displaying the applicable criticality level.

The classification scheme includes for instance a color-coding or a coding or "modulation" by changing size and/or shape of suitable suggestive graphical symbology as indicators. For instance, in one embodiment, the indicators are rendered as disks that have their diameter grow or shrink according to the real-time computed workload and/or non-compliance measures.

In one embodiment the classification scheme is user customizable. In other words, in one embodiment, there is a step S1245 of receiving as user request to customize the classification scheme according to which any one of i) the workload measure, ii) the amount of non-compliance or iii) a measure derived by combining i) and ii) is classified into criticality levels. In one embodiment, the combination of the measures into the single measure is by arithmetical combination, for instance by forming a weighted sum or by forming products.

In one embodiment, the graphics display includes in one embodiment a calendar component and wherein the visual workload measure indication is mapped onto said calendar component.

In sum, it will be appreciated from the above, that the method as proposed herein forms a retrospective, learning-based prediction method of completion times ("due dates") of the individual items of a workflow. The accumulation of predicted due dates does not allow to schedule tasks, but it can be used to indicate whether the start of the workflow of a new patient at a particular day puts pressure on the current and future operations in the department with respect to the active schedules and workflow of other patients, staff members and devices. After the completion of each workflow step, the due date estimation can be automatically updated resulting in improved predictions. Hence, at any point in time a snapshot of a "due date" pressure as measure of a critical workload can be indicated and staff members can react before operations become critical.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A method of supporting task scheduling for one or more processes of various types that use a plurality of resources in a workflow, wherein the plurality of resources include at least devices, equipment, staff members or staff roles, time intervals that are used to schedule tasks, and different categories of resources, the method comprising:
receiving, via a reception workstation, a request for a process of a given type and according to a workflow template, wherein the process of the given type comprises a sequence of tasks to be performed via one or more of the plurality of resources, wherein information regarding an availability of each of the plurality of resources and information about qualifications and availability of staff members is stored in a resource database;
predicting, via a predictor device and based on historical data stored in a database for the historical data, a completion time of a later one of the tasks in the sequence of tasks of the process of the given type, in response to a starting time for a previous one of the tasks in the sequence of tasks of the process of the given type;
mapping, via a mapper device, the predicted completion time across one or more of the different categories of resources, wherein mapping includes (i) computing a work load measure in terms of one of the resource categories and (ii) identifying possible overshoots via a cross-checking of the predicted completion time against a prescribed due-date; and
producing, via a visualizer device and based on the computed work load measure and identified possible overshoots, at least one of a work load focused or due-date focused view of selected ones of the plurality of resources for a given task scheduling arrangement, wherein the work load focused or due-date focused view enables an identification of upcoming bottlenecks in an availability of the plurality of resources.

2. The method of claim 1, further comprising:
re-predicting, via the predictor device, the completion time of the later one of the tasks once any one of the previous tasks in sequence of tasks of the process, or in a co-pending process of a same type, has been completed.

3. The method of claim 1, further comprising:
updating the historical data in the database for the historical data, once one or more tasks, or all tasks, in the sequence of tasks of the process, or of a co-pending process, have been completed.

4. The method of claim 1, further comprising:
establishing, via a validator device, whether the predicted completion time, or a re-predicted completion time, for the later one of the tasks complies with a predefined completion period for said later task.

5. The method of claim 1, further comprising:
predicting respective completion times for two tasks including the later task; and
establishing whether the predicted completion times comply with a predefined lag period between the two tasks.

6. The method of claim 1, further comprising:
for said later task and for a corresponding task in a co-pending process of a same type, accumulating task completion times that i) fall within a given time interval and/or ii) are to be performed by or for the same resource; and
computing a workload measure (i) for the resource and (ii) for the given time interval, from the accumulated task completion times.

7. The method of claim 6, wherein the workload measure is computed in real-time upon any one of i) receiving the request for the process, ii) updating the historical data, iii) updating time constraints applicable to the process type and iv) updating the completion time of any previous task in the process or in the co-pending process.

8. The method of claim 4, further comprising:
displaying, via a graphics display, a visual indication of the workload measure wherein the visual indication varies with a real-time predicted workload measure and/or
displaying, via the graphics display, a visual indication of an amount of non-compliance by which the completion time does not comply with (i) the predefined completion period and/or (ii) the predefined lag time, wherein the visual indication varies with the amount of non-compliance.

9. The method of claim 8, wherein the graphics display includes a calendar component and wherein the visual indication of the workload measure is mapped onto said calendar component.

10. The method of claim 8, wherein the displaying of the graphics display is effected in real-time upon any one of i) receiving the request for the process, ii) updating the historical data, iii) updating time constraints applicable to the process type and iv) updating the completion time of any previous task (a) in the process or (b) in the co-pending process.

11. The method of claim 6, wherein the workload measure for the resource is classified into any one of a plurality of criticality levels according to a classification scheme, wherein the displaying of the visual indication of the workload measure includes displaying an applicable criticality level, and further wherein the classification scheme is user customizable.

12. A system of supporting task scheduling for one or more processes of various types that use a plurality of resources in a workflow, wherein the plurality of resources include at least devices, equipment, staff members or staff roles, time intervals that are used to schedule tasks, and different categories of resources, the system comprising:

an input port (IN) configured to receive a request for a process of a given type and according to a workflow template, wherein the process of the given type comprises a sequence of tasks to be performed via one or more of the plurality of resources, wherein information regarding an availability of each of the plurality of resources and information about qualifications and availability of staff members is stored in a resource database;

a database (HIST-DB) configured to store historical data on previous processes;

a predictor (PR) configured to predict, based on the historical data, a completion time of at least one of the tasks in the sequence of tasks of the process of the given type, in response to a starting time for one of the other tasks in the sequence of tasks of the process of the given type;

a mapper device configured to map the predicted completion time across one or more of the different categories of resources, wherein mapping includes (i) computing a work load measure in terms of one of the resource categories and (ii) identifying possible overshoots via a cross-checking of the predicted completion time against a prescribed due-date;

a graphics display controller (UIC) configured to generate for display at least one visual indicator and based on the computed work load measure and identified possible overshoots, at least one of a work load focused or due-date focused view of selected ones of the plurality of resources for a given task scheduling arrangement, wherein the work load focused or due-date focused view enables an identification of upcoming bottlenecks in an availability of the plurality of resources; and a graphics display screen (M), coupled to the graphics display controller, wherein the graphics display screen is configured to display at least one of the work load focused or due-date focused view.

13. The system of claim 12, wherein the at least one of the plurality of resources comprises a device selected from the group consisting of i) medical imaging modalities, ii) a dedicated treatment preparation workstation and iii) a radiotherapy treatment device.

14. A non-transitory computer readable medium embodied with a computer program of instructions executable by a processing unit of a support system for task scheduling, wherein responsive to execution of the instructions via the processing unit, the processing unit controls the support system to perform the method according to claim 1.

* * * * *